United States Patent
Li et al.

(10) Patent No.: US 10,584,074 B2
(45) Date of Patent: Mar. 10, 2020

(54) MICROENCAPSULATED NITRIFICATION INHIBITOR COMPOSITIONS

(71) Applicant: Dow AgroSciences LLC, Indianapolis, IN (US)

(72) Inventors: Mei Li, Westfield, IN (US); Martin C. Logan, Indianapolis, IN (US); Greg Powels, Carmel, IN (US); Alex Williams, Indianapolis, IN (US); Stephen L. Wilson, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/922,964

(22) Filed: Mar. 16, 2018

(65) Prior Publication Data
US 2018/0265425 A1 Sep. 20, 2018

Related U.S. Application Data

(60) Provisional application No. 62/472,628, filed on Mar. 17, 2017.

(51) Int. Cl.
*C05G 3/08* (2006.01)
*A01N 43/40* (2006.01)
*A01N 25/28* (2006.01)
*A01N 25/04* (2006.01)

(52) U.S. Cl.
CPC ............... *C05G 3/08* (2013.01); *A01N 25/04* (2013.01); *A01N 25/28* (2013.01); *A01N 43/40* (2013.01); *Y02P 60/218* (2015.11)

(58) Field of Classification Search
CPC ........ A01N 25/04; A01N 25/28; A01N 43/40; C05C 1/00; C05C 9/00; C05C 11/00; C05G 3/0017; C05G 3/02; C05G 3/08; Y02P 60/218
See application file for complete search history.

(56) References Cited

U.S. PATENT DOCUMENTS

| 8,263,530 B2 * | 9/2012 | Casana Giner | A01N 25/14 504/127 |
| 2011/0301036 A1 * | 12/2011 | Tank | A01N 25/28 504/347 |
| 2015/0315091 A1 * | 11/2015 | Dave | C05G 3/0017 71/30 |

* cited by examiner

Primary Examiner — John Pak
Assistant Examiner — Nathan W Schlientz

(57) ABSTRACT

The present invention relates to an improved nitrification inhibitor composition and its use in agricultural applications.

14 Claims, No Drawings

MICROENCAPSULATED NITRIFICATION INHIBITOR COMPOSITIONS

FIELD OF THE INVENTION

The present invention relates to improved nitrification inhibitor compositions, methods of making the same, and their use in agricultural applications.

BACKGROUND AND SUMMARY

Nitrogen fertilizer added to the soil is readily transformed through a number of undesirable biological and chemical processes, including nitrification, leaching, and evaporation. Many transformation processes reduce the level of nitrogen available for uptake by the targeted plant. One such process is nitrification, a process by which certain widely occurring soil bacteria metabolize the ammonium form of nitrogen in the soil, transforming the nitrogen into nitrite and nitrate forms, which are more susceptible to nitrogen loss through leaching or volatilization via denitrification.

The decrease in available nitrogen due to nitrification necessitates the addition of more nitrogen rich fertilizer to compensate for the loss of agriculturally active nitrogen available to the plants. These concerns intensify the demand for improved management of nitrogen, in order to reduce costs associated with the use of additional nitrogen fertilizer.

Methods for reducing nitrification include treating soil with agriculturally active compounds that inhibit or at least reduce the metabolic activity of at least some microbes in the soil that contribute to nitrification. These compounds include (trichloromethyl)pyridines, such as nitrapyrin, which have been used as nitrification inhibitors in combination with fertilizers as described in U.S. Pat. No. 3,135,594, the disclosure of which is incorporated herein by reference in its entirety. These compounds help to maintain agriculturally-applied ammonium nitrogen in the ammonium form (stabilized nitrogen), thereby enhancing plant growth and crop yield. These compounds have been used efficaciously with a number of plant crops including corn, sorghum, and wheat.

Compounds such as nitrapyrin are unstable in soil in part because they are very volatile. For example, nitrapyrin has a relatively high vapor pressure ($2.8 \times 10^{-3}$ mm Hg at 23° Celsius), and because of this it has a tendency to volatilize and must be applied immediately or somehow protected from rapid loss after the fertilizer is treated with nitrapyrin. One approach is to add nitrapyrin to a volatile fertilizer, namely anhydrous ammonia, which itself must be added to the soil in a manner that reduces the amount of the volatile active lost to the atmosphere. This method is problematic in that it requires the use of anhydrous ammonia, which is corrosive and must be injected into the soil. This method of applying nitrapyrin, while stabilizing nitrapyrin below the soil surface, is not preferred. This method is unsuitable for many other fertilizer types and their standard application practices such as dry fertilizer granules, which most often are broadcasted onto the soil surface.

Still other approaches to stabilize nitrapyrin and reduce its loss to the atmosphere include applying it to the surface of the soil and then mechanically incorporating it into the soil, or watering it into the soil generally within 8 hours after its application to reduce its loss to the atmosphere. Still another approach is to encapsulate nitrapyrin for rapid or dump release. Such encapsulated forms of nitrapyrin have been formulated with lignin sulfonates as disclosed in U.S. Pat. No. 4,746,513, the disclosure of which is incorporated herein by reference in its entirety. While these formulations are less volatile than simple nitrapyrin, these formulations are better suited for use with liquid urea ammonium nitrate ("UAN") or liquid manure fertilizers than with dry fertilizers. Although the release of nitrapyrin is delayed by the encapsulation, the capsules release all of the nitrapyrin upon contact with moisture, exhibiting the same stability and volatility disadvantages of the prior application methods.

Another approach to stabilizing nitrapyrin includes polycondensation encapsulation. Additional information regarding this approach can be found in U.S. Pat. No. 5,925,464, the disclosure of which is incorporated herein by reference in its entirety. Some of these formulations enhance handling safety and storage stability of the nitrapyrin using polyurethane rather than polyurea to form at least a portion of the capsule shell.

In some instances, polyurea microencapsulation has been used to produce enhanced nitrification inhibitor compositions for delayed, steady release of nitrification inhibitors for application with fertilizers. Such encapsulated forms of nitrapyrin are disclosed in U.S. Pat. Nos. 8,377,849, 8,741,805, and International application PCT/US15/00217 (publication number WO 2016/108928) the disclosures of which are incorporated herein by reference in their entirety.

There remains a need to deliver nitrification inhibitors such as, for example, (trichloromethyl)pyridines in a more efficient manner and with formulations that provide improved storage stability, as measured by decreased crystal formation over longer periods of time, while maintaining a high level of efficacy comparable to unencapsulated nitrification inhibitors.

While aqueous microcapsule suspensions (a.k.a. capsule suspensions or "CS") of nitrapyrin (i.e., microencapsulated nitrapyrin) referred to above are more stable than un-encapsulated nitrapyrin in an aqueous solution under certain conditions, it has been observed that crystals of nitrapyrin can form in the aqueous phase of a microcapsule suspension of nitrapyrin. The weight percentage of crystalline nitrapyrin in the bulk aqueous phase of the microcapsule suspension may accumulate over time. Depending upon how the microcapsule suspensions are handled, the presence of measurable levels of crystalline nitrapyrin in the aqueous phase can be of little-to-no consequence or problematic. The presence of even about 0.1 wt. percent crystalline nitrapyrin or above in the aqueous phase of the microcapsule suspension can be especially problematic if the suspension is applied by spraying the suspension through a fine point nozzle with a sprayer containing inline screens.

Additionally, certain commercial embodiments of polyurea microencapsulated nitrification inhibitors, such as, for example, Instinct® and Entrench® (commercial embodiments sold by Dow AgroSciences LLC), are limited by the amount of active ingredient (nitrification inhibitor) that can be microencapsulated and suspended in the aqueous phase without the active ingredient crystallizing into the aqueous phase. For example, in some embodiments, Instinct® and Entrench® include about 17% to about 19% by weight active ingredient (nitrapyrin). Crystallization of the active ingredient into the aqueous phase has limited using increased levels of active ingredient in these aqueous capsule suspensions. Some commercial nitrapyrin capsule suspension formulations have active loadings of 200 g/L, the upper limit of the loading being bound by the solubility of the nitrapyrin in the solvent used inside of the microcapsules.

In some of the inventive embodiments of the present disclosure, no solvent is required to dissolve the nitrapyrin (and/or other active ingredient) in the lipophilic phase. In some embodiments, stable aqueous capsule suspension formulations with up to about 300 g/L nitrapyrin loading are disclosed, without problematic crystallization issues. In some embodiments of the present disclosure, high-load, aqueous, capsule suspension formulations containing nitrapyrin may include those that contain at least about 150 g/L, at least about 200 g/L, at least about 220 g/L, at least about 240 g/L, at least about 260 g/L, at least about 280 g/L, or at least about 300 g/L of microencapsulated nitrapyrin.

Some aspects of the present disclosure include compositions that prevent and/or reduce crystal formation issues observed in aqueous capsule suspension formulations with up to about 300 g/L nitrapyrin loading such as, for example, those that include at least about 150 g/L, at least about 200 g/L, at least about 220 g/L, at least about 240 g/L, at least about 260 g/L, or at least about 280 g/L of microencapsulated nitrapyrin. Crystal formation in nitrification inhibiting compositions can cause problems including filter blockage during field application of the compositions. In some instances, crystals that form in the liquid phase of a capsule suspension are high purity crystals, comprising substantially pure organic nitrification inhibitor, such as, for example, nitrapyrin. In some instances, high purity nitrapyrin (99 wt %) crystals may form in presently available commercial formulations. Crystal formation, in some instances, is dependent upon the temperature of the formulation during handling, storage, and/or transport of the formulations.

In some embodiments of the microcapsule suspension formulations of the present disclosure, stable, high-load, agricultural liquid formulations comprising aqueous microcapsule suspensions containing low melting active ingredients are presented. In some embodiments, the microcapsule suspension formulations are prepared without use of an organic solvent to dissolve the low melting point active such as, for example, a nitrification inhibitor such as nitrapyrin, and may optionally use small amounts of a polymeric ultra-hydrophobe to prepare the microcapsules. In some embodiments, the nitrapyrin containing microcapsule suspension formulation may include a microencapsulated hydrophobic crystal inhibitor additive to prevent or inhibit crystal formation or growth of the nitrapyrin in the aqueous phase. In some embodiments, the nitrapyrin containing microcapsule suspension formulations that include a microencapsulated hydrophobic crystal inhibitor additive provide superior physical, chemical, and/or crystallization stability upon storage, and acceptable volatility and nitrification inhibition attributes in applications to the soil. In some embodiments, the nitrapyrin containing microcapsule suspension formulation containing the microencapsulated hydrophobic crystal inhibitor additive provide superior physical, chemical, and/or crystallization stability upon storage when compared to those formulations containing only a non-microencapsulated hydrophobic crystal inhibitor additive.

In some embodiments of the microcapsule suspension formulations disclosed herein, post addition (i.e. after nitrapyrin microcapsule formation) of a microencapsulated hydrophobic crystal inhibitor additive to the aqueous phase reduces the rate of crystal formation and/or growth in the aqueous phase during storage. In one embodiment, post addition of one or more microencapsulated hydrophobic crystal inhibitor additives provide superior crystal growth inhibition or reduction during storage. In one exemplary embodiment, post-addition of a microencapsulated hydrophobic crystal inhibitor additive that is an aromatic solvent provides superior crystal growth inhibition or reduction in the aqueous phase of the nitrapyrin containing microcapsule suspension formulation.

The present disclosure therefore provides compositions and methods to prevent and/or reduce crystals and crystal formation in high-load, agricultural active compositions containing organic nitrification inhibitors, such as nitrapyrin. In some embodiments, addition of microencapsulated hydrophobic crystal inhibitor additives prevent and/or reduce crystals and crystal formation in capsule suspensions of microencapsulated nitrapyrin better than when using non-microencapsulated hydrophobic crystal inhibitor additives alone. In some embodiments, microencapsulated hydrophobic crystal inhibitor additives provide superior physical stability to high-load, microencapsulated nitrapyrin formulations at from about 15 to about 55° C. storage conditions.

In certain embodiments, in the absence of the addition of one or more microencapsulated hydrophobic crystal inhibitor additives to the aqueous phase and even with the use of a non-microencapsulated hydrophobic crystal inhibitor additive, high-load microcapsule suspension formulations of nitrapyrin may form problematic levels of nitrapyrin crystals in the aqueous phase at temperatures ranging from about 15° C. to about 55° C. These nitrapyrin crystals may be about 99% pure. Over time, such crystals may compose up to 0.5 weight percent or more of the overall microcapsule suspension formulation. These crystals may form at temperatures such as, for example, 15° C., 20° C., 25° C., 30° C., 35° C., 40° C., 45° C., 50° C., and 55° C. Microencapsulated solvent-based, hydrophobic crystal inhibitor additives such as aromatic solvents and ester compounds can increase the physical stability of high-load microcapsule suspension formulations of nitrapyrin, by preventing or at least reducing crystal formation in the aqueous phase of the microcapsule suspension formulation.

Illustratively, post-added, microencapsulated aromatic solvents used as hydrophobic crystal inhibitor additives may include: Aromatic 100 Fluid, also known as solvent naphtha or light aromatic; Aromatic 150 Fluid, also known as solvent naphtha, heavy aromatic, high flash aromatic naphtha type II, heavy aromatic solvent naphtha, hydrocarbons, C10 aromatics, >1% naphthalene, A150, S150 (Solvesso 150); and Aromatic 200 Fluid, also known as solvent naphtha, heavy aromatic, high flash aromatic naphtha type II, heavy aromatic solvent naphtha, hydrocarbons, C10-13 aromatics, >1% naphthalene, A200, and S200 (Solvesso 200).

The microencapsulated aromatic solvents used in some embodiments, are naphthalene depleted ("ND"), or contain less than about 1% naphthalene. Said microencapsulated solvents may be added to the microcapsule suspension formulation prior to crystal formation as a preventative measure, or added to the microcapsule suspension formulation after crystal formation as a remedial measure to remove or reduce the presence of crystals.

The ester compounds used in some embodiments as microencapsulated hydrophobic crystal inhibitor additives include: 2,2,4-trimethyl-1,3-pentanediol monoisobutyrate.

Additionally, the microcapsule suspension formulations of the present disclosure can be combined or used in conjunction with pesticides, including arthropodicides, bactericides, fungicides, herbicides, insecticides, miticides, nematicides, nitrification inhibitors such as dicyandiamide, urease inhibitors such as N-(n-butyl) thiophosphoric triamide, and the like or pesticidal mixtures thereof. In such applications, the microcapsule suspension formulation of the present disclosure can be tank mixed with the desired pesticide(s) or they can be applied sequentially.

Disclosed herein is a microcapsule suspension formulation comprising: (a) a first suspended phase of a plurality of microcapsules having a volume median particle size of from about 1 to about 10 microns, wherein the microcapsules include: (1) a microcapsule wall produced by an interfacial polycondensation reaction between a polymeric isocyanate and a polyamine to form a polyurea shell; (2) at least one organic nitrification inhibiting compound encapsulated within the polyurea shell; (b) a second suspended phase of a plurality of microcapsules having a volume median particle size of from about 1 to about 10 microns, wherein the microcapsules include: (1) a microcapsule wall produced by an interfacial polycondensation reaction between a polymeric isocyanate and a polyamine to form a polyurea shell; and (2) at least one hydrophobic crystal inhibitor additive encapsulated within the polyurea shell; and (c) an aqueous phase. In some embodiments, the aqueous phase of the microcapsule suspension formulation may further include at least one additional ingredient selected from the group consisting of: non-encapsulated hydrophobic crystal inhibitor additives, dispersants, emulsifiers, rheology aids, antifoam agents, biocides, antifreeze agents, and mixtures thereof.

In some embodiments, the first suspended phase of the plurality of microcapsules in the formulation include 2-chloro-6-(trichloromethyl)pyridine. In other embodiments, the formulation includes between about 15 weight percent and about 40 weight percent 2-chloro-6-(trichloromethyl)pyridine. Still in other embodiments, the formulation includes between about 0.1 weight percent and about 2.00 weight percent of the at least one polymeric ultra-hydrophobe compound contained within the first suspended phase of the plurality of microcapsules. In some embodiments, the at least one polymeric ultra-hydrophobe compound includes polybutene.

In some exemplary embodiments, the aqueous phase of the microcapsule suspension formulation includes between about 1.0 weight percent and about 10.0 weight percent, between about 2.0 weight percent and about 8.0 weight percent, or between about 3.0 weight percent and about 7.0 weight percent of the hydrophobic crystal inhibitor additive which is encapsulated within the second suspended phase of the plurality of microcapsules. In other exemplary embodiments the hydrophobic crystal inhibitor additive is at least one compound selected from the group consisting of: aromatic solvents such as, for example, naphthalene depleted heavy aromatics, and ester compounds such as, for example, 2,2,4-trimethyl-1,3-pentanediol monoisobutyrate, and mixtures thereof.

In some embodiments, the aqueous phase of the microcapsule suspension formulation includes between about 1.0 weight percent and about 10 weight percent of an emulsifier that is a nonionic polymer surfactant. In some embodiments, the nonionic polymer surfactant is selected from the group consisting of: polyvinyl alcohols.

In some embodiments, the aqueous phase of the microcapsule suspension formulation includes at least one additive selected from the group consisting of: modified styrene acrylic polymeric surfactants (i.e., dispersants), polyvinyl alcohols (i.e., emulsifiers) aqueous emulsion of polydimethylsiloxanes (i.e., antifoam agents), xanthan gums (i.e., rheology aids), microcrystalline celluloses (i.e., rheology aids), sodium carboxymethyl-celluloses (i.e., rheology aids), propylene glycol (i.e., an antifreeze agent), a biocide and mixtures thereof. In other embodiments, the formulation includes between about 40 weight percent and about 70 weight percent of the aqueous phase.

Some aspects of the invention include methods for making a microcapsule suspension formulation comprising the steps of: (a) preparing a lipophilic phase comprising at least one lipophilic isocyanate and at least one polymeric ultra-hydrophobe by mixing said at least one lipophilic isocyanate and at least one polymeric ultra-hydrophobe with at least one molten, low melting-point organic nitrification inhibiting compound; (b) preparing an aqueous phase by dissolving and mixing in water at least one additive selected from the group consisting of: dispersants, emulsifiers, antifoams, biocides, and mixtures thereof; (c) combining the lipophilic phase and aqueous phase to form an oil-in-water emulsion; and (d) combining the oil-in-water emulsion with a solution of at least one polyamine in water to generate microcapsules.

In some embodiments of the method, the lipophilic phase includes 2-chloro-6-(trichloromethyl)pyridine. In other embodiments of the method, the lipophilic phase includes between about 75 weight percent and about 90 weight percent 2-chloro-6-(trichloromethyl)pyridine. In other embodiments of the method, the lipophilic phase includes between about 0.1 weight percent and about 3.00 weight percent of the at least one polymeric ultra-hydrophobe compound. Still in other embodiments of the method, the lipophilic phase includes polybutene (i.e., the polymeric ultra-hydrophobe compound).

In some embodiments, the method further includes the step of: adding at least one additive selected from the group consisting of: dispersants, biocides, an aqueous emulsion of polydimethylsiloxane concentrate, a xanthan gum, a microcrystalline cellulose, a carboxymethyl-cellulose sodium, an anti-freeze additive selected from at least one of ethylene glycol, propylene glycol or glycerol, a non-encapsulated hydrophobic crystal inhibitor additive, an aqueous microcapsule suspension containing a microencapsulated hydrophobic crystal inhibitor additive and mixtures thereof, after the step of combining the oil-in-water emulsion with a solution of at least one polyamine in water to generate microcapsules containing nitrapyrin. In other embodiments of the method, the final microcapsule suspension formulation includes between about 1.0 weight percent and about 10.0 weight percent (on a hydrophobic crystal inhibitor additive weight percent basis) of at least one microencapsulated hydrophobic crystal inhibitor additive. In some exemplary embodiments of the method, the hydrophobic crystal inhibitor additive is at least one compound selected from the group consisting of: aromatic solvents, 2,2,4-trimethyl-1,3-pentanediol monoisobutyrate, and mixtures thereof. In some exemplary embodiments of the method, the hydrophobic crystal inhibitor additive is added to the microcapsule suspension formulation as a second microcapsule suspension whereby the hydrophobic crystal inhibitor additive is contained within the microcapsules of the second microcapsule suspension. In some exemplary embodiments of the method, both microencapsulated and non-microencapsulated hydrophobic crystal inhibitor additive may be added to the microcapsule suspension formulation to prevent or inhibit crystal growth.

In still other embodiments of the method, the aqueous phase includes between about 1.0 weight percent and about 10 weight percent of a nonionic polymer surfactant, and in some embodiments, the nonionic polymer surfactant is selected from the group consisting of: polyvinyl alcohols.

In yet other embodiments of the exemplary method, the final microcapsule suspension includes at least one additive selected from the group consisting of: a modified styrene acrylic polymeric surfactant, an aqueous emulsion of polydimethylsiloxane concentrate, a xanthan gum, a microcrystalline cellulose, a carboxymethyl-cellulose sodium, a biocide, a propylene glycol, and mixtures thereof. In some embodiments, the formulation includes between about 40 weight percent and about 70 weight percent of the aqueous phase. In still other embodiments, the method further includes the step of: controlling the temperature of the oil-in-water emulsion while mixing the lipophilic and aqueous phases to produce oily globules of a desired size.

DETAILED DESCRIPTION (Trichloromethyl)pyridine compounds useful in the composition of the present disclosure include compounds having a pyridine ring which is substituted with at least one trichloromethyl group and mineral acid salts thereof. Suitable compounds include those containing chlorine or methyl substituents on the pyridine ring in addition to a trichloromethyl group, and are inclusive of chlorination products of methyl pyridines such as lutidine, collidine and picoline. Suitable salts of the chlorination products of the methyl pyridines include hydrochlorides, nitrates, sulfates and phosphates. The (trichloromethyl)pyridine compounds useful in the practice of the present disclosure are typically oily liquids or crystalline solids. Other suitable compounds are described in U.S. Pat. No. 3,135,594. A preferred (trichloromethyl)pyridine is 2-chloro-6-(trichloromethyl)pyridine, also known as nitrapyrin, and the active ingredient of the product N-SERVE™. (Trademark of Dow AgroSciences LLC).

The utility of compounds such as nitrapyrin has been greatly increased by encapsulating such compounds along with suitable solvents in microcapsules. Especially useful microcapsules include a nitrapyrin/hydrophobic solvent core surround by a polyurea shell. Microcapsules of appropriate volume, shell thickness, and composition can be suspended in, stored in, and applied in an aqueous phase. Such useful formulations are disclosed in U.S. patent application Ser. No. 12/393,661 filed on Feb. 26, 2009, publication number U.S. 2009-0227458 A1 published on Sep. 10, 2009, and now issued as U.S. Pat. No. 8,741,805 issued on Jun. 3, 2014; U.S. patent application Ser. No. 12/009,432, filed Jan. 18, 2008, publication number U.S. 2008-0176745 A1 published on Jul. 24, 2008, and now issued as U.S. Pat. No. 8,377,849 issued on Feb. 19, 2013; and U.S. Provisional Application Ser. No. 60/881,680 filed on Jan. 22, 2007, which are all expressly incorporated by reference herein in their entirety as if each were incorporated by reference individually.

While the microcapsule aqueous suspensions referred to above are more stable than un-encapsulated nitrapyrin in an aqueous solution under certain conditions, it has been observed that crystals of nitrapyrin can form in the aqueous phase of a microcapsule suspension of nitrapyrin.

The weight percentage of crystalline nitrapyrin in the bulk aqueous phase of a microcapsule suspension may accumulate over time. Depending upon how the microcapsule suspensions are handled, the presence of measurable levels of crystalline nitrapyrin in the aqueous phase can be of little-to-no consequence or problematic. The presence of even about 0.1 weight percent or above of crystalline nitrapyrin in the aqueous phase of a microcapsule suspension can be especially problematic if the suspension is applied by spraying the suspension through a fine point nozzle with a sprayer containing inline screens.

Additionally, certain commercial embodiments of capsule suspensions of polyurea microencapsulated nitrification inhibitors, such as, for example, Instinct® or Entrench® (commercial products of Dow AgroSciences LLC), are limited by the amount of active ingredient (nitrification inhibitor) that can be microencapsulated and suspended in the aqueous phase without the active ingredient crystallizing into the aqueous phase. For example, in some embodiments, Instinct® and Entrench® include about 17% to about 19% by weight active ingredient (nitrapyrin). Crystallization of the active ingredient into the aqueous phase has limited the use of increased levels of active ingredient in the capsule suspensions. Some commercial nitrapyrin capsule suspension formulations have active loadings of 200 g/L, the upper limit of the loading being bound by the solubility of the nitrapyrin in a hydrophobic solvent. In some embodiments of the present disclosure, no oil/hydrophobic solvent is required to dissolve the nitrapyrin (and/or other active ingredient) in the lipophilic phase, and aqueous capsule suspensions formulations stable up to 300 g/L nitrapyrin are disclosed, without problematic crystallization issues during extended storage stability testing.

In some embodiments of the microcapsule suspension formulations of the present disclosure, stable, high-load, agricultural liquid formulations comprising aqueous microcapsule suspensions containing low melting active ingredients are presented. In some embodiments, the microcapsule suspension formulations are prepared without use of an organic solvent to dissolve the agricultural active, such as, for example, nitrification inhibitors such as nitrapyrin, by use of a small amount of a polymeric ultra-hydrophobe which is added prior to microcapsule formation and ultimately ends up inside the microcapsule. In some embodiments, a microencapsulated hydrophobic crystal inhibitor additive is post-added to the high-load microcapsule suspension to form formulations that provide superior physical, chemical, and crystallization stability upon storage, and acceptable volatility and nitrification inhibition attributes in applications to the soil.

Exemplary polymeric ultra-hydrophobes include polybutene, such as is commercially available as Indopol® Polybutene Grade: H-15 by INEOS Oligomers. Exemplary nonionic polymers include, but are not limited to, polyvinyl alcohols ("PVA").

Exemplary microencapsulated hydrophobic crystal inhibitor additives (applied during manufacture and/or post-manufacture, "post-addition crystal inhibitor additives") include ester compounds such as 2,2,4-trimethyl-1,3-pentanediol monoisobutyrate, commercially available as UCAR® Filmer IBT (Dow Chemical; Midland, Mich.), and aromatic solvents such as: light aromatics, naphthalene depleted light aromatics, heavy aromatics, and/or naphthalene depleted heavy aromatics, such as, for example, Aromatic 200ND. The encapsulated hydrophobic crystal inhibitor additives may be prepared by using standard polyurea microencapsulation methods that are well known in the art as disclosed herein. In some embodiments, the second suspended phase of the plurality of microcapsules in the microcapsule suspension formulations include a hydrophobic crystal inhibitor additive contained inside of the microcapsules. In other embodiments, the formulation includes between about 0.01 weight percent and about 10.0 weight percent of the hydrophobic crystal inhibitor additive. In another embodiment, the microcapsule suspension formulation may further include from about 0 wt % to about 5 wt % of the non-microencapsulated hydrophobic crystal inhibitor additive in addition to the microencapsulated hydrophobic crystal inhibitor additive.

Exemplary microencapsulated hydrophobic crystal inhibitor additives include aromatic solvents and ester compounds. Microencapsulated hydrophobic crystal inhibitor additives of the present disclosure can be added to capsule suspensions of polyurea microencapsulated nitrapyrin in any weight percent range (on a liquid weight basis) formed between any lower amount including from about 0.01 wt. %, 0.05 wt. %, 0.10 wt. %, 0.25 wt. %, 0.50 wt. %, 0.75 wt. %, and about 1.00 wt. % and any upper amount including about 10.00 wt. %, 7.50 wt. %, 5.00 wt. %, 3.00 wt. %, 2.50 wt. %, 2.00 wt. %, and about 1.50 wt. %.

In some embodiments, the microencapsulated aromatic solvents or ester compounds of the present disclosure can be added to aqueous capsule suspensions of polyurea microencapsulated nitrapyrin in any weight percent range (on a liquid weight basis) selected from the group consisting of: between about 2.00 wt. % and about 3.00 wt. %, between about 1.00 wt. % and about 5.00 wt. %, between about 0.50 wt. % and about 7.50 wt. %, and between about 0.01 wt. % and about 10.00 wt. %.

A broad list of typical solvents and liquid compounds which can be used to dissolve crystalline (trichloromethyl) pyridine compounds and thereby be used as microencapsulated hydrophobic crystal inhibitor additives include aromatic solvents, particularly alkyl substituted benzenes such as xylene or propylbenzene fractions, and mixed naphthalene and alkyl naphthalene fractions; mineral oils; kerosene; dialkyl amides of fatty acids, particularly the dimethylamides of fatty acids such as the dimethyl amide of caprylic acid; chlorinated aliphatic and aromatic hydrocarbons such as 1,1,1-trichloroethane and chlorobenzene; esters of glycol derivatives, such as the acetate of the n-butyl, ethyl, or methyl ether of diethyleneglycol and the acetate of the methyl ether of dipropylene glycol; ester compounds like 2,2,4-trimethyl-1,3-pentanediol monoisobutyrate, ketones such as isophorone and trimethylcyclohexanone (dihydroisophorone); and the acetate products such as hexyl or heptyl acetate. The preferred microencapsulated solvents and compounds which can be used to prevent or inhibit formation of crystalline (trichloromethyl)pyridine compounds are xylene, alkyl substituted benzenes, such as propyl benzene fractions, alkyl naphthalene fractions and 2,2,4-trimethyl-1,3-pentanediol monoisobutyrate.

The nitrapyrin containing microcapsules useful in the present disclosure can be prepared by the polycondensation reaction of a polymeric isocyanate and a polyamine to form a polyurea shell. Methods of microencapsulation are well known in the art and any such method can be utilized in the present disclosure to provide the capsule suspension formulation. In general, the capsule suspension formulation can be prepared by first mixing a polymeric isocyanate with a (trichloromethyl)pyridine, and/or other low-melting point agricultural active, and optionally, an ultra-hydrophobic compound such as a polymeric ultra-hydrophobe. This mixture is then combined with an aqueous phase, which optionally includes an emulsifier to form a two phase system. The organic phase is emulsified into the aqueous phase by shearing until the desired particle size is achieved. An aqueous crosslinking polyamine solution is then added dropwise while stirring to form the encapsulated particles of (trichloromethyl)pyridine in an aqueous suspension. Alternatively, an oil-in-water emulsion can be added to an aqueous solution of a polyamine under shearing to form the microcapsules. In some embodiments, the microcapsules of the present disclosure can be prepared by a batch processing method, a continuous processing method, or a combination of a batch process and a continuous process.

The desired particle size and cell wall thickness will depend upon the actual application. The nitrapyrin containing microcapsules typically have a volume median particle size of from about 1 to about 10 microns and a capsule wall thickness of from about 50 to about 125 nanometers. In another embodiment, requiring soil surface stability, the desired particle size may be from about 1-5 microns, with cell wall thicknesses of from about 75 to about 125 nanometers. The microcapsules containing the hydrophobic crystal inhibitor additive typically have a volume median particle size of from about 1 to about 10 microns and a capsule wall thickness of from about 10 to about 40 nanometers or from about 20 to about 30 nanometers.

Other conventional additives may also be incorporated into the exemplary formulations such as, for example, emulsifiers, dispersants, thickeners, biocides, antifreeze agents, pesticides, salts and film-forming polymers.

Dispersing and emulsifying agents, known as surface-active agents or surfactants, include condensation products of alkylene oxides with phenols and organic acids, alkyl aryl sulfonates, modified styrene acrylic polymeric surfactants, polyoxyalkylene derivatives of sorbitan esters, complex ether alcohols, mahogany soaps, lignin sulfonates, polyvinyl alcohols, and the like. The surface-active agents are generally employed in the amount of from about 1 to about 20 percent by weight of the microcapsule suspension formulation.

The weight ratio of the suspended phases to the aqueous phase within the microcapsule suspension formulation of the present disclosure is dependent upon the desired concentration of (trichloromethyl)pyridine compound in the final formulation. Typically, the weight ratio will be from about 1:0.75 to about 1:20. Generally the desired ratio is about 1:1 to about 1:7, and is preferably from about 1:1 to about 1:4. The ratio may also be in the range of about 1:1 to about 1:2.

The presence of a (trichloromethyl)pyridine compound suppresses the nitrification of ammonium nitrogen in the soil or growth medium by inhibiting the activity of certain microbes present in the soil, thereby preventing the rapid loss of ammonium nitrogen from sources such as nitrogen fertilizers, organic nitrogen constituents, and/or organic fertilizers and the like.

Generally, the microcapsule suspension formulations of the present disclosure are applied such that the (trichloromethyl)pyridine compound is applied to the soil or a growth medium at a rate of from about 0.5 to about 1.5 kg/hectare, preferably at a rate of from about 0.58 to about 1.2 kg/hectare. The preferred amount can be ascertained by the application preference, considering factors such as soil pH, temperature, soil type and mode of application.

The microcapsule suspension formulations of the present disclosure can be applied in any manner which will benefit the crop of interest. In one embodiment, the microcapsule suspension formulation is applied to growth medium in a band or row application. In another embodiment, the formulation is applied to or throughout the growth medium prior to seeding or transplanting the desired crop plant. In yet another embodiment, the formulation can be applied to the root zone of growing plants.

Additionally, the microcapsule suspension formulation can be applied with the application of nitrogen fertilizers. The formulation can be applied prior to, subsequent to, or simultaneously with the application of fertilizers.

The microcapsule suspension formulations of the present disclosure have the added benefit that they are stable enough that they can be applied to the soil surface, without having to immediately add additional water or using mechanical incorporation in order to mix the formula into the soil; in some embodiments the formula can reside on the surface of the soil for days or even weeks. Alternatively, if desired, the formulations of the present disclosure can be incorporated into the soil directly upon application.

The microcapsule suspension formulations of the present disclosure typically have a concentration of (trichloromethyl)pyridine compound in amounts of from about 5, preferably from about 10 and more preferably from about 15 to about 40, typically to about 35, preferably to about 30 and more preferably to between about 25 percent by weight and 27 percent by weight, based on the total weight of the microcapsule suspension formulation. The microcapsule suspension formulations are then optionally mixed with one or more solvents and/or water to obtain the desired rate for application.

Soil treatment compositions may be prepared by dispersing, coating, or impregnating the microcapsule suspension formulation into or onto fertilizers such as ammonium or organic nitrogen fertilizer. The resulting fertilizer composition may be employed as such or may be modified, as by dilution with additional nitrogen fertilizer or with inert solid carrier to obtain a composition comprising any desired amount of active agent for treatment of soil.

The soil may be prepared in any fashion with the microcapsule suspension formulations of the present disclosure, including mechanically mixed with the soil; applied to the surface of the soil and thereafter dragged or diced into the soil to a desired depth; or by being directly transported into the soil by method such as by: injection, spraying, dusting or irrigation. In irrigation applications, the formulations may be introduced to irrigation water in an appropriate amount in order to obtain a distribution of the (trichloromethyl)pyridine compound to the desired depth of up to 6 inches (15.24 cm.).

Surprisingly, once incorporated into the soil, the microcapsule suspension formulations of the present disclosure outperform other nitrapyrin formulations, especially unencapsulated versions. It was thought that the encapsulated composition would not release nitrapyrin sufficiently to be as effective as the non-encapsulated versions, wherein the diffusion from the capsule would be too slow to provide a biological effect, but in fact, the opposite effect is observed.

The controlled release of nitrapyrin in the microcapsule suspension formulations of the present disclosure exhibits certain advantages over the application of unencapsulated nitrapyrin. First, the amount of nitrapyrin can be reduced since it is more efficiently released into the soil over an extended period of time. Secondly, if desired, the microcapsule suspension formulations of the present disclosure can be applied and left on the surface to be naturally incorporated into the soil, without the need for mechanical incorporation.

In some embodiments, the microencapsulated hydrophobic crystal inhibitor additives are added to the aqueous phase of microcapsule suspension formulations that include nitrapyrin in order to reduce the rate of nitrapyrin crystal formation and/or growth in the aqueous phase at certain temperature and/or storage conditions. In some embodiments, microencapsulated hydrophobic crystal inhibitor additives added after the formation of nitrapyrin crystals has occurred, may provide both crystal reduction and crystal growth reduction under temperature and/or storage conditions known to promote nitrapyrin crystal growth. In some exemplary embodiments, the microencapsulated hydrophobic crystal inhibitor additives include at least one oil and are added to the aqueous phase of the formulations after the formation of the nitrapyrin containing microcapsules.

In some cases, microcapsule suspension formulations may already include crystals of nitrapyrin before any hydrophobic crystal inhibitor additives can be added to the aqueous phase. These suspensions may be treated with one or more encapsulated and/or non-encapsulated hydrophobic crystal inhibitor additives by adding them to the aqueous phase of the suspension to reduce or eliminate the crystals over a period of time.

Formulations of the present disclosure include capsule suspension concentrates of microcapsules suspended in aqueous solution, wherein the microcapsules include at least one low-melting point agricultural active ingredient and at least one ultra-hydrophobic compound. The aqueous phase may include at least one nonionic polymer, and, at least one or more microencapsulated hydrophobic crystal inhibitor additives that are post-added to the formulations to stabilize the crystal growth issues of active ingredients in the continuous aqueous phase. High-load nitrapyrin capsule suspensions containing greater than about 150 g/L, greater than about 200 g/L, greater than about 220 g/L, greater than about 240 g/L, greater than about 260 g/L, greater than about 280 g/L, or greater than about 300 g/L active ingredient may form nitrapyrin crystals in the aqueous phase at temperatures of from about 15° C. to about 55° C. The nitrapyrin crystals may be about 99% pure. Under some conditions, over time, such crystals may compose up to 0.5 weight percent or more of the overall microcapsule suspension formulations. Crystals may form at temperatures including, for example, 15° C., 20° C., 25° C., 30° C., 35° C., 40° C., 45° C., 50° C., and 55° C. The microencapsulated hydrophobic crystal inhibitor additives described herein provide superior physical stability, by preventing or reducing crystal formation in the aqueous phase of the high-load nitrapyrin microcapsule suspension formulations over longer periods of time than do the non-microencapsulated hydrophobic crystal inhibitor additives.

Illustratively, post-added microencapsulated hydrophobic crystal inhibitor additives that are aromatic solvents include: Aromatic 100 Fluid, also known as solvent naphtha or light aromatic; Aromatic 150 Fluid, also known as solvent naphtha, heavy aromatic, high flash aromatic naphtha type II, heavy aromatic solvent naphtha, hydrocarbons, C10 aromatics, >1% naphthalene, A150, S150 (Solvesso 150); and Aromatic 200 Fluid, also known as solvent naphtha, heavy aromatic, high flash aromatic naphtha type II, heavy aromatic solvent naphtha, hydrocarbons, C10-13 aromatics, >1% naphthalene, A200, and S200 (Solvesso 200).

The microencapsulated aromatic solvents, in some embodiments, are naphthalene depleted ("ND"), or contain less than about 1% naphthalene. Said microencapsulated solvents can be added to the microcapsule suspension formulation prior to crystal formation as a preventative measure, or added to the microcapsule suspension formulation after crystal formation as a remedial measure to remove or reduce the presence of crystals.

The exemplary microcapsule suspension formulations of the present disclosure may further include any combination of stabilizers, thickeners, dispersants, biocides, surfactants, plasticizers, and/or solvents known to those of ordinary skill in the art to adapt the viscosity, flowability, density, thickness, and/or stability of the formulations.

Additionally, the microcapsule suspension formulations of the present disclosure can be combined or used in conjunction with pesticides, including arthropodicides, bactericides, fungicides, herbicides, insecticides, miticides, nematicides, nitrification inhibitors such as dicyandiamide, urease inhibitors such as N-(n-butyl) thiophosphoric triamide, and the like or pesticidal mixtures and mixtures thereof. In such applications, the microcapsule suspension formulation of the present disclosure can be tank mixed with the desired pesticide(s) or they can be applied sequentially.

Exemplary herbicides include, but are not limited to acetochlor, alachlor, aminopyralid, atrazine, benoxacor, bromoxynil, carfentrazone, chlorsulfuron, clodinafop, clopyralid, dicamba, diclofop-methyl, dimethenamid, fenoxaprop, flucarbazone, flufenacet, flumetsulam, flumiclorac, fluroxypyr, glufosinate-ammonium, glyphosate, halosulfuron-methyl, imazamethabenz, imazamox, imazapyr, imazaquin, imazethapyr, isoxaflutole, quinclorac, MCPA, MCP amine, MCP ester, mefenoxam, mesotrione, metolachlor, s-metolachlor, metribuzin, metsulfuron methyl, nicosulfuron, paraquat, pendimethalin, picloram, primisulfuron, propoxycarbazone, prosulfuron, pyraflufen ethyl, rimsulfuron, simazine, sulfosulfuron, thifensulfuron, topramezone, tralkoxydim, triallate, triasulfuron, tribenuron, triclopyr, trifluralin, 2,4-D, 2,4-D amine, 2,4-D ester and the like.

Exemplary insecticides include, but are not limited to 1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha cypermethrin, alpha ecdysone, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate, barium hexafluorosilicate, barthrin, benclothiaz, bendiocarb, benfuracarb, benoxafos, bensultap, benzoximate, benzyl benzoate, beta cyfluthrin, beta cypermethrin, bifenazate, bifenthrin, binapacryl, bioallethrin, bioethanomethrin, biopermethrin, bistrifluron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuform, chloromethiuron, chloropicrin, chloropropylate, chlorphoxim, chlorprazophos, chlorpyrifos, chlorpyrifos methyl, chlorthiophos, chromafenozide, cinerin I, cinerin II, cis-methrin, cloethocarb, clofentezine, closantel, clothianidin, copper acetoarsenite, copper arsenate, copper naphthenate, copper oleate, coumaphos, coumithoate, crotamiton, crotoxyphos, cruentaren A &B, crufomate, cryolite, cyanofenphos, cyanophos, cyanthoate, cyclethrin, cycloprothrin, cyenopyrafen, cyflumetofen, cyfluthrin, cyhalothrin, cyhexatin, cypermethrin, cyphenothrin, cyromazine, cythioate, d-limonene, dazomet, DBCP, DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfiram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma cyhalothrin, gamma HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, ometothoate, oxamyl, oxydemeton methyl, oxydeprofos, oxydisulfoton, paradichlorobenzene, parathion, parathion methyl, penfluron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfiram, sulfluramid, sulfotep, sulfur, sulfuryl fluoride, sulprofos, tau fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidothion, vamidothion, vaniliprole, vaniliprole, XMC, xylylcarb, zeta cypermethrin and zolaprofos.

Additionally, any combination of one or more of the above pesticides can be used.

Additionally, Rynaxypyr™ (trademark of DuPont), an anthranilic diamide (Chlorantraniliprole) crop protection chemistry can be used to practice the invention.

As used throughout the specification, the term "about" refers to plus or minus 10% of the stated value, for example the term 'about 1.0' includes values from 0.9 to 1.1.

The following examples are provided to illustrate the present invention. The examples are not intended to limit the scope of the present invention and they should not be so interpreted. Amounts are in weight parts or weight percentages unless otherwise indicated.

EXAMPLES

High-load nitrapyrin capsule suspension formulations containing hydrophobic crystal inhibitor additives (microencapsulated and/or non-microencapsulated) were prepared by microencapsulation of oil-in-water emulsions. Samples with 1) 2.4 to 5.3 wt % of non-microencapsulated Aromatic 200 ND; 2) 5.0 to 6.7 wt % (liquid basis) of microencapsulated Aromatic 200 ND in the presence of from 0 to 2.4 wt % of non-microencapsulated Aromatic 200 ND; 3) 4.8 wt % of non-microencapsulated Aromatic 150 ND; and 4) 5.0 to 7.0 wt % (liquid basis) of microencapsulated Aromatic 100 ND, were prepared as described.

Aromatic 200 ND (or Aromatic 100 ND) microcapsule suspension (CS) preparation procedure: The composition of Aromatic 200 ND (or Aromatic 100 ND) microcapsule suspension composition is listed in Table 1. The oil phase was prepared by mixing Aromatic 200 ND solvent (or Aromatic 100 ND) and PAPI 27 at ambient temperature. The aqueous phase was prepared by mixing PVA, Metasperse 500L, Proxel GXL, and antifoam at ambient temperature. The oil phase was then combined with the aqueous phase and passed through a high shear device for emulsification targeting a desired number average particle size diameter (D50) of 3 microns. Then, the aqueous ethylene diamine solution was added to the emulsion at proper mixing conditions to form the Aromatic 200 ND (or Aromatic 100 ND) microcapsule suspension.

TABLE 1

Composition of Aromatic 200 ND (or Aromatic 100ND) Capsule Suspension

| Component | Source | Wt % |
| --- | --- | --- |
| Aromatic 200 ND (or Aromatic 100 ND) | Exxon Mobile | 50.0 |
| PAPI-27 Polymeric MDI | Dow Chemical | 1.68 |
| Ethylene Diamine (30%) | Huntsman | 1.23 |
| PVA (Selvol 205 21% sol.) | Brennteg | 10.4 |
| Metasperse 500L | Croda | 0.9 |
| Antifoam | Harcros | 0.14 |
| Proxel | Arch Chemicals | 0.11 |
| Water as balance | Local Source | 35.54 |
| Total | | 100 |

Preparation of the nitrapyrin capsule suspension concentrate (CSC): The composition of the nitrapyrin CSC is listed in Table 2. The oil phase was prepared by mixing nitrapyrin tech., Indopol H and PAPI 27 at 75 to 100° C. The aqueous phase was prepared by mixing PVA, Metasperse 500L, Proxel GXL, water and antifoam at 60 to 90° C. The oil phase was then combined with the aqueous phase and processed with a high shear mixing device for emulsification targeting a desired number average particle size diameter (D50) of about 3 microns. Then, the aqueous ethylene diamine solution was added to the emulsion with low shear mixing to form the nitrapyrin capsule suspension concentrate (CSC).

TABLE 2

Composition of Nitrapyrin Capsule Suspension Concentrate (CSC)

| Component | Source | Wt % |
| --- | --- | --- |
| Nitrapyrin | Dow AgroSciences | 38.2 |
| PAPI-27 Polymeric MDI | Dow Chemical | 8.0 |
| Ethylene Diamine (30%) | Huntsman | 6.3 |
| PVA (Selvol 205 21% sol.) | Brennteg | 9.8 |
| Metasperse 500L | Croda | 2.9 |
| Indopol H-15 | Ineos Olefins and Polymers | 1.0 |
| Antifoam | Harcros | 0.1 |
| Proxel | Arch Chemicals | 0.1 |
| Water as balance | Local Source | 33.6 |
| Total | | 100 |

High-load nitrapyrin capsule suspension sample preparation: The nitrapyrin capsule suspension concentrate (CSC) was mixed with Kelzan S (as 1.5 or 2.0 wt % aqueous solution), propylene glycol, Aromatic 200 ND solvent (or Aromatic 150 ND solvent), and/or the pre-made A-200 ND capsule suspension, or the pre-made A-100 ND capsule suspension, and the balance of the water to form the final compositions. Samples prepared in this manner are listed in Table 3. Samples 1, 2, control A and control B used the same batch of CSC. Samples 3, 4, control C, and control D used another batch of CSC. Samples 5 and 6 used a 3rd batch of CSC.

TABLE 3

Composition of High-Load Nitrapyrin Capsule Suspensions

| Sample | Nitrapyrin CSC[1] | Non-microencapsulated A-200 ND solvent | A-200 ND capsule suspension | Non-microencapsulated A-150 ND solvent | A-100 ND capsule suspension | Propylene glycol | Kelzan S (1.5% solution) | Kelzan S (2% solution) | Balance water |
|---|---|---|---|---|---|---|---|---|---|
| 1 | 66.90% | 0% | 10.00% | 0% | 0% | 10.3% | 10.0% | 0% | 2.8% |
| 2 | 67.20% | 2.40% | 10.00% | 0% | 0% | 10.0% | 10.0% | 0% | 0.4% |
| 3 | 68.00% | 0% | 10.20% | 0% | 0% | 10.0% | 10.3% | 0% | 1.5% |
| 4 | 67.90% | 0% | 13.40% | 0% | 0% | 8.2% | 10.4% | 0% | 0% |
| 5 | 68.60% | 0% | 0% | 0% | 10% | 10.0% | 0% | 7.4% | 4.0% |
| 6 | 68.60% | 0% | 0% | 0% | 14% | 10.0% | 0% | 7.4% | 0% |
| control A | 67.90% | 2.80% | 0% | 0% | 0% | 10.0% | 10.1% | 0% | 9.2% |
| control B | 69.40% | 5.20% | 0% | 0% | 0% | 10.4% | 0% | 7.1% | 7.9% |
| control C | 68.10% | 5.30% | 0% | 0% | 0% | 10.6% | 0% | 3.6% | 12.2% |
| control D | 69.40% | 0% | 0% | 4.80% | 0% | 10.1% | 10.5% | 0% | 5.3% |

[1]The amount of nitrapyrin contained in the listed samples ranges from 25.55 wt % to 26.51 wt %.

Samples 1, 2, 3, 4, 5, and 6 in Table 3 contain microencapsulated hydrophobic crystal inhibitor additives and were tested for crystallization stability at different time intervals and at different temperatures and are compared against control samples A, B, C, and D, which contained only liquid hydrophobic crystal inhibitor additive, but no microencapsulated crystal inhibitor additive. Some of the tests were conducted by seeding the samples with small amounts of washed sea sand particles (from Fisher Scientific) to aid crystal formation. The results of wet sieve testing these samples are summarized in Table 4. Samples containing the encapsulated hydrophobic crystal inhibitor additives showed only minimal amounts (<0.1 wt %) of non-crystalline residue, whereas the 4 control samples (A, B, C, and D) containing only liquid hydrophobic crystal inhibitor additives (i.e., non-encapsulated hydrophobic crystal inhibitor additives) showed the formation of problematic levels (>0.1 wt %) of crystalline residue. The presence of crystalline solids in the test samples after storage can be easily determined by examination with a microscope using polarizing light.

Referring to Table 4, the wet sieve procedure for determining the crystal content in the storage samples was carried out as follows: approximately 20 g of sample were added to a glass beaker containing between 100 and 200 grams of tap water. The solution was stirred using a glass stir rod and then poured through a 100 mesh sieve (149 μm). The beaker was rinsed with additional water and the rinse was also poured through the sieve. Tap water was poured over the sample in the sieve for approximately 30 seconds to rinse weak agglomerates through. The residual left on the screen was rinsed onto a tared filter paper and vacuum filtered. This filter paper with sample was allowed to dry in a lab hood for at least four hours and then reweighed. Residue percentages were calculated using equation (1):

$$\text{Residue Percentage} = (\text{Filter paper and Residue Weight After Drying (g)} - \text{Filter Paper Weight (g)})/(\text{Total Sample Sieved (g)}). \quad (1)$$

TABLE 4

Accelerated Storage Stability Test Results - Wet Sieve Residue Analysis 100 mesh Wet Sieve Residue (wt %): <0.1 wt % & No Crystals = Pass

| Sample | 2-wk Ambient (non-seeded) | 2-wk Ambient (seeded) | 2-wk 54° C. (non-seeded) | 2-wk 54° C. (seeded) | 4-wk 40° C. (non-seeded) | 8-wk 40° C. (non-seeded) | Crystal Formation Observed | Test Result |
|---|---|---|---|---|---|---|---|---|
| 1 | 0.07%[1] | 0.09%[1] | 0.07%[1] | 0.09%[1] | 0.06%[1] | 0.07%[1] | no | pass |
| 2 | 0.07%[1] | 0.08%[1] | 0.07%[1] | 0.09%[1] | 0.07%[1] | 0.07%[1] | no | pass |
| 3 | 0.06%[1] | n/t | 0.05%[1] | 0.03%[1] | 0.03%[1] | 0%[1] | no | pass |
| 4 | 0.05%[1] | n/t | 0.06%[1] | n/t | 0.03%[1] | 0%[1] | no | pass |
| 5 | n/t | 0% | n/t | 0.06%[1] | n/t | n/t | no | pass |
| 6 | n/t | 0% | n/t | 0.06%[1] | n/t | n/t | no | pass |
| control A | 0.05%[1] | n/t[3] | 0.06%[1] | n/t | 0.24%[2] | n/t | yes | fail |
| control B | 0.07%[1] | 0.09%[1] | 0.08%[1] | 0.14%[2] | 0.07%[1] | 0.08%[1] | yes | fail |
| control C | 0.06%[1] | n/t | 0.06%[1] | 0.1%[2] | 0.05%[1] | 0.14[2] | yes | fail |
| control D | 0.06%[1] | n/t | 0.12%[2] | n/t | 0.03%[1] | 0%[1] | yes | fail |

[1]non-crystalline solids formed;
[2]crystalline solids formed;
[3]n/t not tested.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

The invention claimed is:

1. A stable microcapsule suspension formulation including:
    (a) a first suspended phase of a plurality of microcapsules having a volume median particle size of from about 1 to about 10 microns, wherein the microcapsules include:
        (1) a microcapsule wall produced by an interfacial polycondensation reaction between a polymeric isocyanate and a polyamine to form a polyurea shell; and
        (2) at least one organic nitrification inhibiting compound selected from the group consisting of (trichloromethyl)pyridine compounds encapsulated within the polyurea shell;
    (b) a second suspended phase of a plurality of microcapsules having a volume median particle size of from about 1 to about 10 microns, wherein the microcapsules include:
        (1) a microcapsule wall produced by an interfacial polycondensation reaction between a polymeric isocyanate and a polyamine to form a second polyurea shell; and
        (2) at least one hydrophobic crystal inhibitor additive encapsulated within the second polyurea shell; and
    (c) an aqueous phase;
    wherein the aqueous phase includes from 0 to 2.4% by wt. of non-microencapsulated hydrophobic crystal inhibitor, and less than 0.1% by wt. of crystals when stored at 40° C. for 4 weeks.

2. The microcapsule suspension formulation according to claim 1, wherein the aqueous phase further includes an additional ingredient selected from the group consisting of: dispersants, emulsifiers, rheology aids, antifoam agents, biocides, antifreeze agents and mixtures thereof.

3. The microcapsule suspension formulation according to claim 2, wherein the organic nitrification inhibiting compound includes 2-chloro-6-(trichloromethyl)pyridine.

4. The microcapsule suspension formulation according to claim 3, wherein the formulation includes between about 15 weight percent and about 40 weight percent of the 2-chloro-6-(trichloromethyl)pyridine.

5. The microcapsule suspension formulation according to claim 2, wherein the aqueous phase includes between about 1.0 weight percent and about 10 weight percent of the emulsifier.

6. The microcapsule suspension formulation according to claim 5, wherein the emulsifier is a nonionic polymer surfactant selected from the group consisting of: polyvinyl alcohols.

7. The microcapsule suspension formulation according to claim 2, wherein the dispersant is a modified styrene acrylic polymeric surfactant.

8. The microcapsule suspension formulation according to claim 1, wherein the formulation further includes an agricultural active ingredient selected from the group consisting of: arthropodicides, bactericides, fungicides, herbicides, insecticides, miticides, nematicides, fertilizers, dicyandiamide, urease inhibitors, and pesticidal mixtures thereof.

9. The microcapsule suspension formulation according to claim 1, further including at least one polymeric ultra-hydrophobe compound.

10. The microcapsule suspension formulation according to claim 9, wherein the polymeric ultra-hydrophobe compound includes polybutene.

11. The microcapsule suspension formulation according to claim 1, wherein the formulation includes between about 1.0 weight percent and about 10.0 weight percent of the microencapsulated hydrophobic crystal inhibitor additive.

12. The microcapsule suspension formulation according to either of claim 1, wherein the hydrophobic crystal inhibitor additive is a compound selected from the group consisting of aromatic solvents and 2,2,4-trimethyl-1,3-pentanediol monoisobutyrate.

13. The microcapsule suspension formulation according to claim 12, wherein the aromatic solvents include light aromatics, naphthalene depleted light aromatics, heavy aromatics, and/or naphthalene depleted heavy aromatics.

14. The microcapsule suspension formulation according to claim 1, wherein the formulation includes between about 40 weight percent and about 70 weight percent of the aqueous phase.

* * * * *